United States Patent [19]
Boebel

[11] Patent Number: 5,127,918
[45] Date of Patent: Jul. 7, 1992

[54] LATCHING DEVICE FOR HANDLES OF MEDICAL INSTRUMENTS

[75] Inventor: Manfred Boebel, Oetisheim, Fed. Rep. of Germany

[73] Assignee: Richard Wolf GmbH, Knittlingen, Fed. Rep. of Germany

[21] Appl. No.: 560,531

[22] Filed: Jul. 31, 1990

[30] Foreign Application Priority Data

Sep. 22, 1989 [DE] Fed. Rep. of Germany ....... 3931577

[51] Int. Cl.⁵ ............................................. A61B 17/28
[52] U.S. Cl. ..................................... 606/208; 81/322; 433/160
[58] Field of Search ................ 606/83, 119, 120, 174, 606/205–211, 148; 81/415, 417, 322, 323, 324, 325; 294/99.2, 100; 433/159, 160, 4

[56] References Cited

U.S. PATENT DOCUMENTS

| | | | |
|---|---|---|---|
| 632,843 | 9/1899 | McGhee | 433/159 |
| 943,263 | 12/1904 | Moraweck | 606/205 |
| 1,174,004 | 2/1916 | Greenwald | 606/210 |
| 1,886,121 | 11/1932 | Silvis | 606/210 |
| 2,652,832 | 9/1953 | Castroviejo | 81/322 |

FOREIGN PATENT DOCUMENTS

| | | | |
|---|---|---|---|
| 179273 | 8/1954 | Austria | 81/322 |
| 3110666 | 11/1982 | Fed. Rep. of Germany | 606/210 |
| 3223513 | 12/1983 | Fed. Rep. of Germany | 606/207 |

*Primary Examiner*—C. Fred Rosenbaum
*Assistant Examiner*—William W. Lewis
*Attorney, Agent, or Firm*—Panitch Schwarze Jacobs & Nadel

[57] ABSTRACT

A latching device for enabling pieces of tissue or foreign bodies to be held securely by medical forceps during a medical operation comprises two elongate spring members whose opposed ends are secured in closed, telescoping tubes which are hinged to the handles of a forceps. The forceps handles are elastically yielding to some degree and by closing them together the spring members are moved towards one another and are caused to hook together by means of butting faces. Hence the tissue or the like which the forceps has taken hold of is automatically held secure once the manual pressure on the handle has been relaxed. If the handles are pressed closer together, the hooked interengagement is released and the spring-loading in the forceps handles opens them and allows the forceps jaws to release the tissue or the like which is being held.

6 Claims, 2 Drawing Sheets

LATCHING DEVICE FOR HANDLES OF MEDICAL INSTRUMENTS

BACKGROUND OF THE INVENTION a) Field of the Invention

In medical practice, forceps are often used in endoscopic operations to enable pieces of tissue or the like to be taken hold of and removed. When this is done it is important to ensure that the pieces taken hold of are firmly held by the instrument during the operation.

b) Description of the Prior Art

There are known latching devices for the handles of medical instruments, i.e. forceps, which can be closed together against spring-loading, such as those described in U.S. patent specification 4644 651, DE-PS 32 23 513 and DE-GM 83 16 034.

In contrast to the known latching devices, the object of the invention is so to design a medical instrument, such as a grasping forceps, having handles closable together against spring-loading, that the jaws of the forceps are held in position by handles which can be closed together with only one hand and so that the latching device used is protected against damage and creates no risk of injury to the user.

SUMMARY OF THE INVENTION

To this end, the present invention consists in a latching device for forceps handles which are elastically yielding to some degree and can be closed together against spring-loading, characterised by two elongated spring members which are secured to two telescoping tubes connected to the ends of the forceps handles, which members are provided with pairs of faces extending parallel to one another and inclined at an angle to the longitudinal axis, one of which pairs, after the spring members have moved towards one another for a certain distance, engaging one behind the other at the same time as the resistance at a first point of resistance is overcome, in which position the two handles are latched, and in that, after a certain additional distance has been travelled and at the same time as the resistance at a second point of resistance is overcome, the two ends of the spring members return in the region of cutouts to the original position in which their axes were parallel and, as the force acting on the two spring-loaded handles is relaxed, slide over one another and release the engagement between the two spring members and thus unlatch the two handles.

Preferably, the spring members are flat in configuration and one said face of one of the spring members is created by a hook-shaped projection.

In one embodiment of the invention, that end of the spring member which carries the face which is created by the hook-shaped projection is formed to be longer in the longitudinal direction than an end of the other spring member.

Advantageously, the two telescoping tubes which receive the spring members are connected together telescopically either directly or via one or more intermediate tubes.

One of the telescoping tubes may have one or more spring elements to allow the engaged position to be identified.

By means of the invention it is possible to operate the forceps easily with only one hand and yet allow the forceps to hold tissue or the like securely. Moreover, the latching device and the parts thereof are protected against damage by being housed in the telescoping tubes, which also protects the user from being injured by the latching device.

BRIEF DESCRIPTION OF THE DRAWINGS

In order that the invention may be more readily understood, an embodiment thereof will now be described, by way of example, with reference to the accompanying drawings, in which.

DESCRIPTION OF THE PREFERRED EMBODIMENT

Figure 2B:
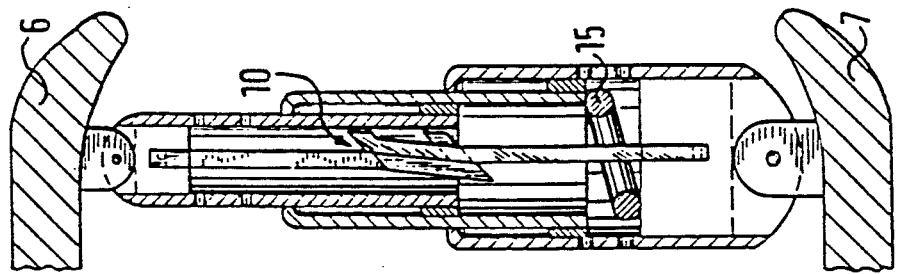

Referring to the drawings, a latching device for holding forceps jaws or the like in a closed position comprises two flat spring members 1 and 2, the ends of which are secured in telescoping tubes 3 and 4 which are connected by an intermediate tube 5. The closed, mutually opposed ends of tubes 3 and 4 are hinged to the two handles 6 and 7 of a forceps. The handles are elastically yielding to some degree.

At their free ends 8,9, the spring members 1,2 extend into parallel, inclined butting faces 10 and 11 which on one side project above the thickness of the spring members 1 and 2, with a hook face 12 following on from butting face 11. This hook face 12 on spring member 1 co-operates with a butting face 13 on end 8 of spring member 2 as soon as the two spring members are moved towards one another by closing together the two handles 6,7, because the butting faces 10,11 bend spring members 1,2 out of straight until butting face 13 hooks over hook face 12. This ensures that the jaws of the forceps, which may for example be gripping pieces of tissue or foreign bodies, are fixed satisfactorily in the closed position.

To reach the closed position (engaged position), it is necessary to overcome the resistance at a first point of resistance resulting from the force which has to be exerted to distort the spring members 1,2.

If the jaws of the forceps are to be released from this closed position, the handles 6,7 which are elastically yielding to some degree, should be brought closer together until butting face 13 on spring member 2 is in a position where it is behind butting face 14 on spring member 1. If handles 6,7 are released at this point, their spring loading will spread them apart and as a result the two spring members 1,2 will be drawn apart at the same time as the telescoping tubes 3,4,5 are opened out. The two spring members 1,2 will move in directions perpendicular to their planes, due to the butting faces 13,14 sliding over one another, and will escape from one another.

To rule out as far as possible any likelihood of the handle being accidently closed to the disengaging position, a spring member 15 is mounted in telescoping tube 4. What this does is to ensure that a perceptible resistance has to be overcome to pass from the engaged to the disengaging position, thus allowing the user easily to feel that the instrument is in the engaged position.

Thus, to bring the latching device to the disengaging position, a second point of resistance has to be overcome and a distance defined by the configuration of end 9 of spring member 2 has to be travelled, for which purpose end 9 of spring member 1 is made longer in the longitudinal direction than end 8 of spring member 2.

Figure 2A:
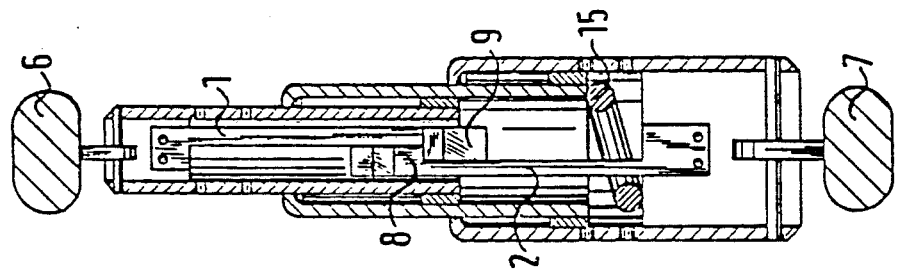
Figure 3A:
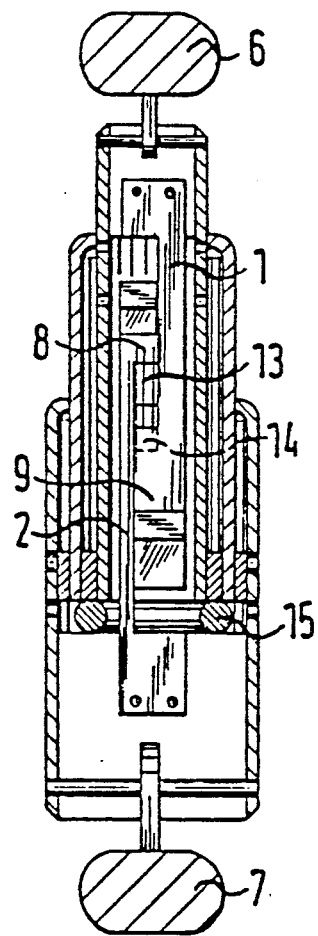
FIGS. 3a and 3b shows the latching device in the position in which the two spring members disengage.
Figure 3B:
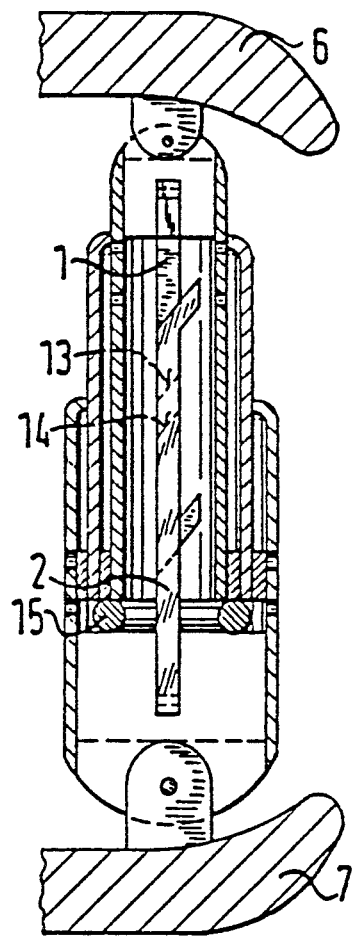

The engaged position is shown in FIG. 2 and FIG. 3 shows the position for releasing the engaged spring members (the disengaging position).

Figure 1B:
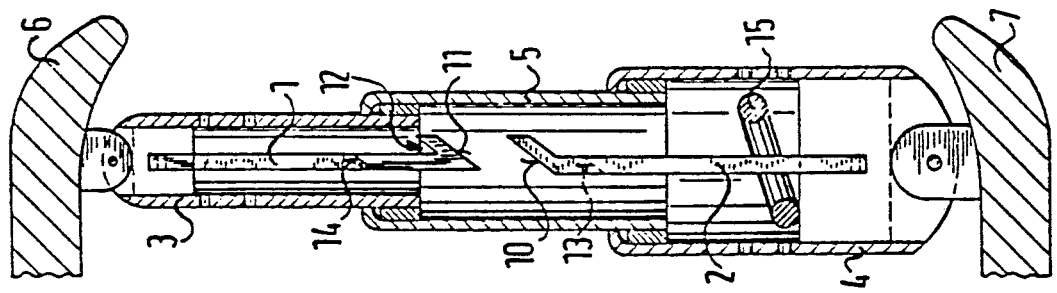
FIGS. 1a and 1b shows two views, orientated at 90 to one another, of the parts of a latching device composed of the two spring members, with a telescoping shell which houses the latching device shown in section, FIGS. 2a and 2b consists, of two views, similar to those in FIGS. 1a and 1b, once the two spring members have attained the engaged state.
Figure 1A:
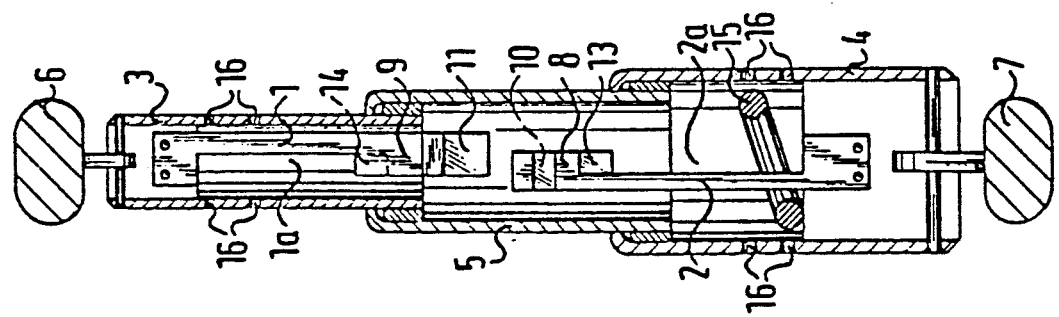

As the spring members 1,2 are slid towards one another from the position shown in FIG. 1, to that seen in FIG. 2, they are guided in telescoping tube 3 by virtue of the fact that the inside diameter of the tube is only slightly larger than the width of one end of the spring members.

Telescoping tubes 3 and 4 are provided with slots 16 which make it possible for any liquid which may have penetrated into them, in the course of sterilization for example, to drain out.

Whilst a particular embodiment has been described, it should be appreciated that the invention is not limited thereto but includes all modifications and variations falling within its scope.

I claim:

1. A latching device for forceps handles which are elastically yielding to some degree and can be closed together against spring-loading, characterized by two elongate spring members which are secured to two telescoping tubes having a longitudinal axis and connected to the forceps handles, said spring members being provided with pairs of faces extending parallel to one another and inclined at an angle to the longitudinal axis, one of which pairs, after the spring members have moved towards one another for a certain distance, engaging one behind the other at the same time as the resistance at a first point of resistance is overcome, in which position the two forceps handles are latched, and in that, after a certain additional distance has been travelled and at the same time as the resistance at a second point of resistance is overcome, two ends of the spring members return in the region of cutouts to their original position in which their axes were parallel and, as a force acting on the two spring-loaded forceps handles is relaxed, slide over one another and release the engagement between the two spring members and thus unlatch the two forceps handles.

2. A latching device according to claim 1, wherein the spring members are substantially flat in configuration and one said face of one of the spring members is created by a hook-shaped projection.

3. A latching device according to claim 2, wherein that end of the spring member which carries the face which is created by the hook-shaped projection is formed to be longer in the longitudinal direction than an end of the other spring member.

4. A latching device according to claim 1, wherein the two telescoping tubes which receive the spring members are directly connected together telescopically.

5. A latching device according to claim 1, wherein the two telescoping tubes which receive the spring members are connected together telescopically via at least one intermediate tube.

6. A latching device according to claim 1, wherein one of the telescoping tubes has at least one spring element to allow the engaged position to be identified.

* * * * *